US00PP21931P2

(12) United States Plant Patent
Sal

(10) Patent No.: US PP21,931 P2
(45) Date of Patent: May 24, 2011

(54) *COREOPSIS* PLANT NAMED 'MOONRAY'

(50) Latin Name: *Coreopsis verticillata*
Varietal Denomination: Moonray

(75) Inventor: Eric M. Sal, Hamilton, MI (US)

(73) Assignee: Walters Gardens Inc., Zeeland, MI (US)

( * ) Notice: Subject to any disclaimer, the term of this patent is extended or adjusted under 35 U.S.C. 154(b) by 6 days.

(21) Appl. No.: 12/586,959

(22) Filed: Sep. 30, 2009

(51) Int. Cl.
*A01H 5/00* (2006.01)

(52) U.S. Cl. ..... Plt./417

(58) Field of Classification Search ..... Plt./263, Plt./417
See application file for complete search history.

(56) References Cited

U.S. PATENT DOCUMENTS

PP19,311 P2 * 10/2008 Walters et al. ..... Plt./417
* cited by examiner

*Primary Examiner* — Susan B McCormick Ewoldt

(57) ABSTRACT

The new and distinct Threadleaf Coreopsis, *Coreopsis verticillata* plant named 'Moonray', with narrow linear or deeply dissected tri-lobed foliage, numerous flowers of pale creamy yellow un-fringed petals having rounded apices and long flowering season from early summer until frost.

1 Drawing Sheet

Botanical designation: *Coreopsis verticillata.*
Cultivar denomination: 'Moonray'.

BACKGROUND OF THE PLANT

The present invention relates to the new and distinct Threadleaf *Coreopsis* herein also referred to as *Coreopsis verticillata* 'Moonray', by the cultivar name, Moonray, or as the new plant. 'Moonray' was discovered by Eric M. Sal in June of 2002 as an uninduced whole plant mutation of *Coreopsis* 'Moonbeam' (not patented) in the fields of a wholesale perennial grower based in Zeeland, Mich., USA. It was then isolated and compared in subsequent years to other *coreopsis* and found to be different from all cultivars known to the discoverer.

Asexual propagation at the same nursery in Zeeland, Mich., USA by cuttings has shown 'Moonray' to be stable and reproduce true to type in successive generations.

SUMMARY OF THE PLANT

The Plant has not been observed in all possible environmental conditions. The phenotype may vary slightly with changes in environments such as light intensity, fertility, water availability, etc. without, however any variation in genotype.

*Coreopsis* 'Moonray' is distinct from all known cultivars in the following traits:

1. Narrow foliage with moderate height.
2. Petite flowers held above the foliage with light creamy ray petals.
3. Long flowering period.

Plants of *Coreopsis* 'Moonray' are most similar to *Coreopsis* 'Sunbeam' U.S. Plant Pat. No. 19,311, 'Zagreb' (not patented) and *Coreopsis* 'Moonbeam' (not patented). In comparison, 'Zagreb' is the shortest and also has a darker flower than 'Moonray'. The other three, 'Moonbeam', 'Mooonray' and 'Sunbeam' all have similar plant habit and size, similar foliage types and long seasonal bloom, but 'Sunbeam' has the darkest yellow-gold flower petals, 'Moonray' the lightest creamy yellow flowers of the three, and 'Moonbeam' has flowers that are in between in yellow intensity.

BRIEF DESCRIPTION OF THE DRAWINGS

The color photographs illustrate the overall characteristics of the Plant. The colors are as true as reasonably possible given the technology available. The color values may vary slightly depending on light intensity and quality.

DETAILED BOTANICAL DESCRIPTION

Figure 1:
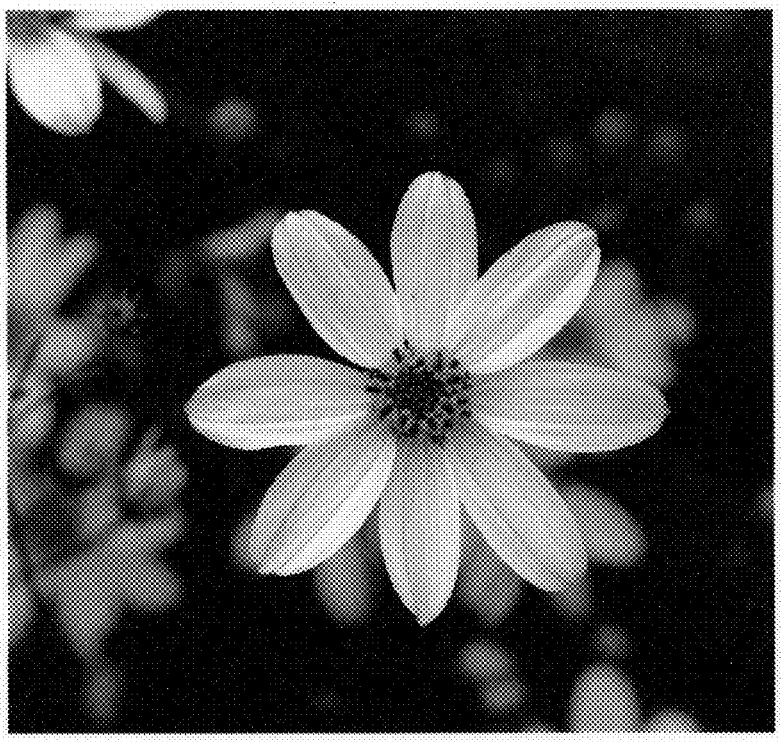
FIG. 1 shows a close-up of the flower of the new plant.
Figure 2:
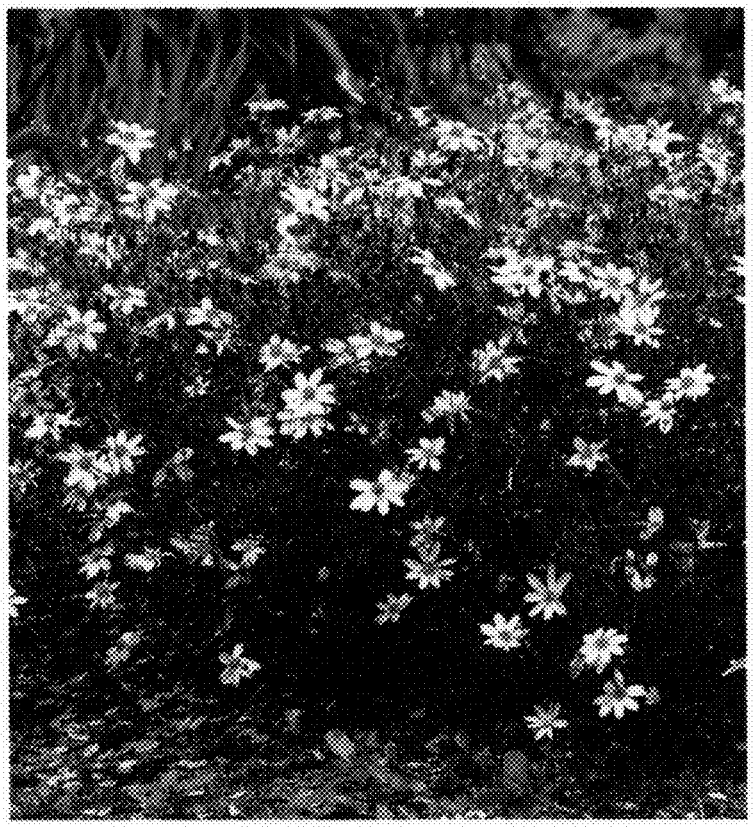
FIG. 2 shows the new plant in a landscape environment.

The following description is based on a three-year old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2001 edition.

Parentage: Non-induced mutation of 'Moonbeam' (not patented).

Asexual propagation: Cuttings, about 10 to 14 days to initiate roots; time to finish as # 1 field grown, 9 months;

Plant habit: Freely basally and axillarily branched, rounded, herbaceous perennial mound; 50 to 60 cm wide, 50 to 55 cm tall;

Leaves: Opposite, linear and entire to deeply dissected tri-lobed, glabrous, acute apex; base attenuate; petiolulate; up to 3 cm long and 2 mm wide; RHS 135A on top and RHS 139A on lower surfaces;

Veins: Not obvious;

Flower: Composite consisting of ray and disc florets; on terminal branches; 3.5 cm diameter, 1.0 cm tall from outer set of involucral bracts to top of disc florets; fragrance not detected;

Phyllary: Sepals in two distinct whorls, outer whorl consisting of about 10, acute apex, narrowly deltoid, truncate base, glabrous, of variable length between 2 and 4 mm long and 1 mm wide at base, between RHS 139B and RHS 137A on both sides; inner whorl sepals tight against ray petals, usually 8 in number, 6 mm long and 2 mm wide, acute apex and truncate base, closest to RHS 161A at apex and RHS 144A at base;

Flowering period: Early summer through frost; producing over 40 flowers per stem and over 200 flowers per plant;

Flower longevity: 5 to 8 days;

Flower buds: One to two days before showing ray petal color spherical with slightly flattened top, 4.0 mm wide and 4.0 mm diameter; lighter than RHS 152D and more green than RHS 161A;

Peduncle: Glaucous, thin, wiry, strong, many branched; 5.0 mm wide at base; RHS 147B;

Pedicel: Glaucous, thin, wiry, strong; about 0.5 mm in diameter, 4 to 5 cm long, color closest to RHS 137A.

Ray florets: Usually 8 per flower; oblong elongate, apex rounded, margin entire; base narrowly cuneate; opening to form 180° angle; parallel veined; glabrous on both surfaces, 1.4 to 1.7 cm long and 6 to 7 mm wide; color opening to between RHS 4B and RHS 4C and lightening to RHS 4D on both surfaces; corolla tube about 2.0 mm long; containing only gynoecium with pistil 2 to 3 mm long and split stigma; both pistil and stigma color between RHS 8C and RHS 8B;

Disc florets: 30 to 60 per head; consisting of tepals, staminal tube and pistil; size about 7 mm long by 1 mm wide at top;

Tepals: Five; 5 mm long and 1 mm wide, fused in the basal 4 mm, acute apex, tepal color nearest RHS 152 D;

Staminal tube: Made up of five fused stamens, 3 to 4 mm long, staminal tube color darker than either RHS N186A or RHS N200A;

Anther: About 1 mm long, closest to RHS 187A;

Pollen: Fine, round, closest to RHS 21C;

Style: About 4.5 mm long; RHS 160B;

Stigma: Split in half and curling back as it matures; stigma color between RHS 8C and RHS 8B;

Seed: Has not yet been observed; *Coreopsis verticillata* 'Moonray' is tolerant of winter temperatures as low as −20° C. and summer temperatures as high as 40° C. Once established it is also tolerant of dry summer conditions but does best with ample moisture and good drainage. It is not known to be tolerant of diseases and pest that are common to other *Coreopsis* cultivars.

I claim:

1. The new and distinct cultivar of *Coreopsis* plant named 'Moonray' as described and illustrated, with pale creamy yellow un-fringed petals, fine thread-like foliage and long flowering season and useful as a specimen landscape plant, mass planting or cut flower.

* * * * *